(12) United States Patent
Lim

(10) Patent No.: US 11,503,869 B2
(45) Date of Patent: Nov. 22, 2022

(54) ARTIFICIAL HAIR AND METHOD OF MANUFACTURING THE SAME

(71) Applicant: HUMAN WELLNESS INC, Seoul (KR)

(72) Inventor: Sin Young Lim, Seoul (KR)

(73) Assignee: HUMAN WELLNESS INC, Seoul (KR)

( * ) Notice: Subject to any disclaimer, the term of this patent is extended or adjusted under 35 U.S.C. 154(b) by 379 days.

(21) Appl. No.: 16/623,491

(22) PCT Filed: Aug. 23, 2018

(86) PCT No.: PCT/KR2018/009750
§ 371 (c)(1),
(2) Date: Dec. 17, 2019

(87) PCT Pub. No.: WO2019/088428
PCT Pub. Date: May 9, 2019

(65) Prior Publication Data
US 2021/0282486 A1 Sep. 16, 2021

(30) Foreign Application Priority Data
Nov. 1, 2017 (KR) .......................... 10-2017-0144417

(51) Int. Cl.
*A61F 2/10* (2006.01)
*A41G 5/00* (2006.01)
(Continued)

(52) U.S. Cl.
CPC ................ *A41G 5/006* (2013.01); *A61F 2/10* (2013.01); *A61L 27/18* (2013.01); *D01D 5/12* (2013.01);
(Continued)

(58) Field of Classification Search
CPC ..... A61F 2/10; A61F 2240/001; A41G 5/006; A61L 27/18; D01D 5/12
(Continued)

(56) References Cited

U.S. PATENT DOCUMENTS 9,993,334 B1 * 6/2018 Loria .......................... A61F 2/10
10,682,223 B2 * 6/2020 Loria .......................... A61F 2/10
(Continued)

FOREIGN PATENT DOCUMENTS

CA         2777234 C  *  2/2019  ........... A61L 24/046
IL           250281 A  *  6/2021  ......... A61B 17/3468
(Continued)

*Primary Examiner* — Suzette J Gherbi
(74) *Attorney, Agent, or Firm* — Patent Office of Dr. Chung Park

(57) ABSTRACT

The present invention provides an artificial hair and a method for producing same. The method for producing an artificial hair according to the present invention comprises: a step of mixing polyamide 6 powder and a master batch at a predetermined weight ratio; a step of drawing an artificial hair from the mixture; a step of forming a loop part by knotting a distal end of the drawn artificial hair; a step of cutting the distal end of the artificial hair, leaving just 1-1.5 mm from the knotted part of the loop part; a step of trimming the artificial hair to a predetermined length after the cutting; and a step of bundling a plurality of the trimmed artificial hair.

5 Claims, 9 Drawing Sheets

(51) Int. Cl.
*D01D 5/12* (2006.01)
*D01F 1/04* (2006.01)
*D01F 6/60* (2006.01)
*A61L 27/18* (2006.01)
*A61B 17/00* (2006.01)

(52) U.S. Cl.
CPC ................ *D01F 1/04* (2013.01); *D01F 6/60* (2013.01); *A61B 2017/00752* (2013.01); *A61F 2240/001* (2013.01)

(58) Field of Classification Search
USPC ...................................................... 623/15.11
See application file for complete search history.

(56) References Cited

U.S. PATENT DOCUMENTS

| | | | |
|---|---|---|---|
| 10,925,718 B2 * | 2/2021 | Loria | A41G 5/008 |
| 2019/0117378 A1 * | 4/2019 | Loria | A41G 5/008 |
| 2021/0161649 A1 * | 6/2021 | Loria | A41G 5/008 |
| 2022/0061981 A1 * | 3/2022 | Loria | A61F 2/10 |

FOREIGN PATENT DOCUMENTS

| | | | | |
|---|---|---|---|---|
| JP | 9206321 A | | 8/1997 | |
| JP | 2022524508 A | * | 5/2017 | ........... A61F 24/046 |
| JP | 3211650 U | | 7/2017 | |
| KR | 20-0342236 Y1 | | 2/2004 | |
| KR | 10-1084492 B1 | | 11/2011 | |
| KR | 20220082403 A | * | 1/2014 | ............... A61F 2/10 |
| KR | 20-0473555 Y1 | | 6/2014 | |
| KR | 10-1623231 B1 | | 5/2016 | |

* cited by examiner

ARTIFICIAL HAIR AND METHOD OF MANUFACTURING THE SAME

CROSS-REFERENCE TO RELATED APPLICATIONS

This application is a national stage application of International Patent Application No. PCT/KR2018/009750 filed on Aug. 23, 2018, which claims priority to Korean Patent Application No. 10-2017-0144417 filed on Nov. 1, 2017, the entire contents of which are incorporated by reference herein.

TECHNICAL FIELD

The present invention relates to an artificial hair and a method of manufacturing the same, and more particularly to an artificial hair implanted into the scalp and a method of manufacturing the artificial hair.

BACKGROUND

In general, the hair loss occurs due to aging of the human body, drug abuse, or psychological stress.

When the hair loss occurs, many people use wigs or receive hair implant by surgical operation to cover the hair loss.

Among these, many people have an interest in hair implant because the hair implant can maintain a natural hair condition in spite of the economic burden, and various hair implant procedures are being recently performed.

For this reason, in recent years, various studies are being conducted on hairs and methods of directly implanting hairs into the human body.

For example, in regard to the material of hair for implant, nylons, polyesters, synthetic resins, etc., which have relatively little effect of rejection reaction in the body after hair implant, are being used.

Meanwhile, in regard to the hair implant method, studies on implant methods using various implant members which can maintain natural hair without falling out after hair implant while not giving sense of difference to the hair implant area are being conducted.

Among such hair implant methods, Korean Patent No. 10-1623231 (title: hair implant anchors and systems and methods for use thereof, hereinafter referred to as 'prior art document 1') discloses a hair implant method in which a hair and a scalp tissue are mechanically and artificially connected by providing an anchor connecting a natural hair or an artificial hair to a tissue of the human.

However, in the hair implant method disclosed in the prior art document 1, the branch of the anchor is formed of a shape memory material, a high elastic material, an elastic plastic material or a super absorbent polymer, or at least one of the branch and the holder is formed of nitinol (alloy material), causing physiological side effects.

In addition, inflammation, infection, etc. of the anchor (implant) cannot be excluded at all, and when there is a need to remove the anchor due to inflammation, infection, etc., there is a significant difficulty in removing the anchor (implant).

SUMMARY

Accordingly, the present disclosure provides an artificial hair and method of manufacturing the artificial hair, which can minimize the side effects caused by typical anchors or implants by directly implanting an artificial hair for implant into the scalp.

In one general aspect, a method of manufacturing an artificial hair implanted in a scalp includes: mixing polyamide 6 powder and a master batch in a certain weight ratio; drawing the artificial hair from a mixture of the polyamide 6 powder and the master batch; forming a ring portion by knotting an end of the drawn artificial hair; cutting the end of the artificial hair, leaving about 1 mm to about 1.5 mm from a knot portion of the ring portion; cutting the artificial hair into a certain length after the cutting of the end of the artificial hair; and collecting a plurality of cut artificial hairs into a set, wherein: the ring portion is inserted and buried into a hairy fascia of the scalp; the diameter of the ring portion is set within a range of about 0.6 mm to about 1.2 mm such that the ring portion is insertable into the hairy fascia; the ring portion is coupled to the hairy fascia; the artificial hear is implanted using an implant device including a head coupled and fixed to a body and an implant needle provided to enter and exit the head while the ring portion is fitted on an end portion thereof drawn from the head; the head has an end portion thereof making contact with the scalp and having an inclined surface; and the implant needle entering and exiting the inclined surface of the head is drawn to implant the artificial hair while being biased to a long end portion of the head.

The polyamide 6 powder and the master batch in the mixing of the polyamide 6 powder and the master batch may be mixed in a weight ratio of about 90 to 100:about 10 to 0.

The master batch may be further mixed with a pigment, and the pigment may include any one or two or more of black, yellow and red dyes.

In the forming of the ring portion, the ring portion may be formed by two or more knot portions, and the knot portion may be ultrasonically fused and fixed.

On the other hand, it is possible to achieve the above object through the artificial hair manufactured by the manufacturing method as described above.

Other features and aspects will be apparent from the following detailed description, the drawings, and the claims.

According to an artificial hair and a method of manufacturing the same, by directly implanting the artificial hair for implant in the scalp, the rejection reaction of the human body such as infection or inflammation caused by typical anchors or implants can be minimized, and the replacement of the artificial hair can be easily performed.

DETAILED DESCRIPTION OF THE DISCLOSURE

Hereinafter, exemplary embodiments of the present invention will be described in detail with reference to the accompanying drawings.

Terms used in the present disclosure are terms defined in consideration of functions in the present disclosure, which may vary according to a user's intention or an operator's intention or custom, and thus, definitions of these terms are intended to be consistent with the technical matters of the present disclosure.

In particular, the term "and/or" used in the present disclosure is used in the meaning including at least one or more of the components listed before and after, and "one or more" means one or plurality of two or more.

In addition, optional terms such as "first", "second", "one side", and "other side" used in the present disclosure are used to distinguish one component from another component, and the component is not limited by the terms described above.

In the present disclosure, "formed on" and "formed on the side surface" do not mean only that the corresponding components are directly stacked in contact with each other, but also mean that other components are further formed between the corresponding components. For example, "formed on" means that the second component is formed in direct contact with the first component and the third component is further formed between the first component and the second component.

FIGS. 1 to 9 are views illustrating an artificial hair implant device and components thereof according to an embodiment of the present invention.

Figure 1:
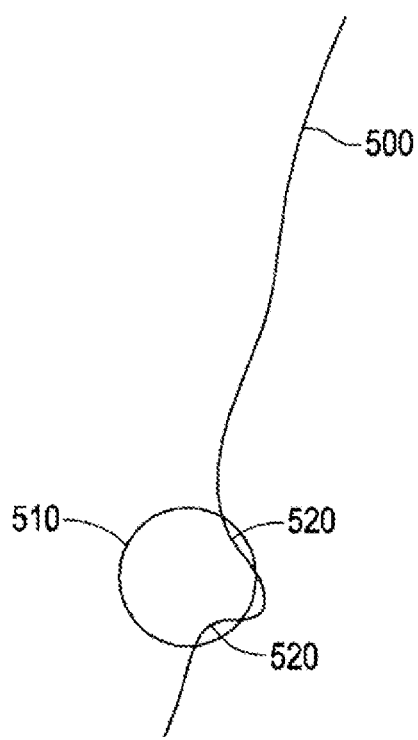
FIG. 1 is a view illustrating an artificial hair according to an embodiment of the present invention.

As shown in FIG. 1, an artificial hair 500 according to an embodiment of the present invention is drawn and formed one by one, and the artificial hair 500 formed as described above is knotted by twisting one end thereof, thereby forming a circular ring portion 510 at one end of the 500.

As described above, the ring portion 510 formed by the knot includes a plurality of knot portions 520 for forming the ring portion 510 to prevent loosening, and each knot portion 520 at which the artificial hair 500 is twisted is provided to be fused and fixed by an ultrasonic wave.

In particular, since the ring portion 510 of the artificial hair 500 formed as described above is inserted and buried into the hairy fascia of the scalp (see FIG. 9), the end of the ring portion 510 of the artificial hair 500 is cut off, leaving only about 1 mm to about 1.5 mm.

Here, the remaining length of the end of the ring portion 510 is a minimum length for preventing the loosening of the knot portion 520. If the remaining length is less than about 1 mm, the end portion forming the knot portion 520 may not maintain knotting with the ring portion 510 and may become loose. Also, if the remaining length exceeds about 1.5 mm, the end of the ring portion 510 is unnecessarily long, causing entangling with other surrounding ring portions when buried in the hairy fascia. Accordingly, it is most desirable to leave the length of the end of the ring portion 510 to be about 1 mm to about 1.5 mm.

In addition, the diameter of the ring portion 510 formed as described above may be formed to range from about 0.6 mm to about 1.2 mm. That is, if the diameter of the ring portion 510 is less than about 0.6 mm, the hairy fascia is not sufficiently filled in the inside of the ring portion 510 and thus a binding force between the hairy fascia and the ring portion 510 is weak when the ring portion 510 is buried in the hairy fascia. Also, if the diameter of the ring portion 510 exceeds about 1.2 mm, the binding force between the ring portion 510 and the hairy fascia is improved, but the ring portion 150 may be entangled with other surrounding ring portions due to the large diameter of the ring portion 510, and the process of implanting the ring portion 510 through the scalp is not smooth. Accordingly, it is most desirable that the diameter of the ring portion 510 be formed to be about 0.6 mm to about 1.2 mm.

On the other hand, the method of manufacturing the artificial hair 500 includes a raw material mixing operation S1, a drawing operation S2, a ring forming operation S3, a fusion operation S4, a ring end cutting operation S5, a cutting operation S6, an artificial hair setting operation S7, and a packing operation S8 are included.

In the raw material mixing operation S1, polyamide 6 powder and master batch are mixed in a certain weight ratio. The polyamide 6 powder and the master batch are mixed in a weight ratio of 90 to 100:10 to 0. Here, polyamide is ordinary nylon, which has good oil resistance, abrasion resistance and hydrophilic property, and the master batch is a compounding agent for improving the dispersibility of a pigment mixed in the polyamide 6 powder. The master batch mixed in the polyamide 6 powder further includes a certain proportion of pigment with respect to 100 parts by weight of the master batch. The pigment includes any one or two or more of black, yellow, and red dyes. Accordingly, if no master batch is mixed with the polyamide 6 powder (if 0 weight %), a black artificial hair 500 is manufactured.

Then, in the drawing operation S2, a single fiber, i.e., a single strand of artificial hair 500 having a diameter of 80 microns is extracted from the mixture of the polyamide 6 powder and the master batch.

In ting forming operation S3, a circular ring portion 510 is formed by knotting one end of the strand of artificial hair 500 that is drawn. In this case, a knot portion 520 forming the ring portion 510 may be formed at least in plurality to prevent the loosening of the ring portion 510 to the maximum.

On this other hand, the diameter of the ring portion 510 formed as described above may be formed to range from about 0.6 mm to about 1.2 mm. If the diameter of the ring portion 510 is less than about 0.6 mm, the hairy fascia is not sufficiently filled in the inside of the ring portion 510 and thus a binding force between the hairy fascia and the ring portion 510 is weak when the ring portion 510 is buried in the hairy fascia. Also, if the diameter of the ring portion 510 exceeds about 1.2 mm, the binding force between the ring portion 510 and the hairy fascia is improved, but the ring portion 150 may be entangled with other surrounding ring portions due to the large diameter of the ring portion 510, and the cut part of the scalp becomes large in the process of implanting the ring portion 510. Accordingly, it is most desirable that the diameter of the ring portion 510 be formed to be about 0.6 mm to about 1.2 mm.

In the fusion operation S4, each knot portion 520 forming the ring portion 510 of the artificial hair 500 formed in the ring forming operation S3 is instantaneously fused and fix by an ultrasonic wave. The ultrasonic fusion operation S4 may be performed only for the knot portion 520 of the ring portion 510, and the knot portion 520 ultrasonically fused may be hardened and fixed in a knotted state, thereby preventing loosening of the knot 520.

In the ring end cutting operation S5, the remaining length of the one end of the ring portion 510 of the artificial hair 500 is cut off, leaving only about 1 mm to about 1.5 mm. Here, the order of ring end cutting operation S5 and fusion operation S4 may be changed.

On the other hand, the remaining length of the end of the ring portion 510 is a minimum length for preventing the loosening of the knot portion 520. If the remaining length is less than about 1 mm, the end portion forming the knot portion 520 may not maintain knotting with the ring portion 510 and may become loose. Also, if the remaining length exceeds about 1.5 mm, the end of the ring portion 510 is unnecessarily long, causing entangling with other surrounding ring portions when buried in the hairy fascia. Accordingly, it is most desirable to leave the length of the end of the ring portion 510 to be about 1 mm to about 1.5 mm.

In the cutting operation S6, after one end of the artificial hair 500 forming the ring portion 510 in the ring end cutting operation S5 is cut, the length of the artificial hair 500 on the opposite side is cut to a length of the required product. The artificial hair 500 to be cut in this way may be cut to a length of about 15 cm to about 30 cm according to the length of the product, and may be cut to any other length.

In the artificial hair setting operation (S7), the artificial hair 500 having undergone cutting operation S6 is collected into one set of about three to five strands. By setting a plurality of artificial hairs 500 as described above, the hair looks rich when the artificial hair 500 is implanted.

In the packing operation S8 the artificial hair sets are arranged in a certain number and then packed.

On the other hand, the artificial hair 500 formed by the manufacturing method as described above is implanted in the scalp through a dedicated implant device 100.

Figure 3:
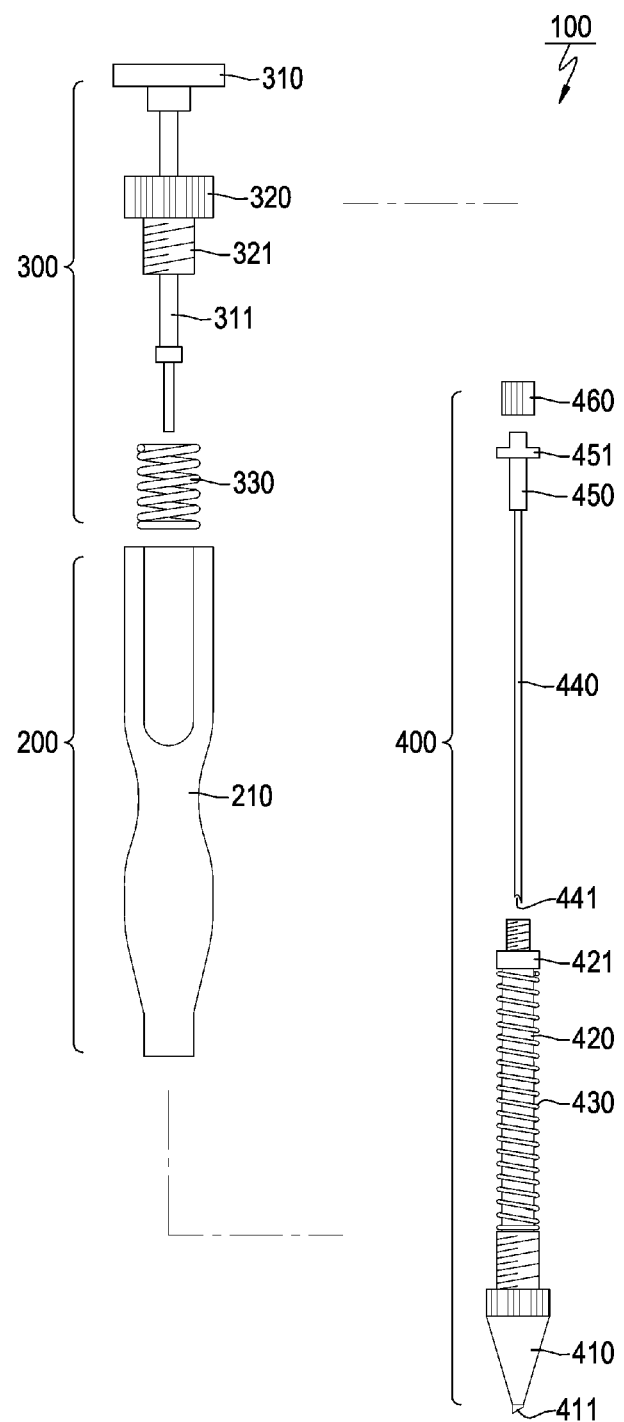
FIG. 3 is an exploded view illustrating an implant device for implanting an artificial hair according to an embodiment of the present invention.
Figure 4:
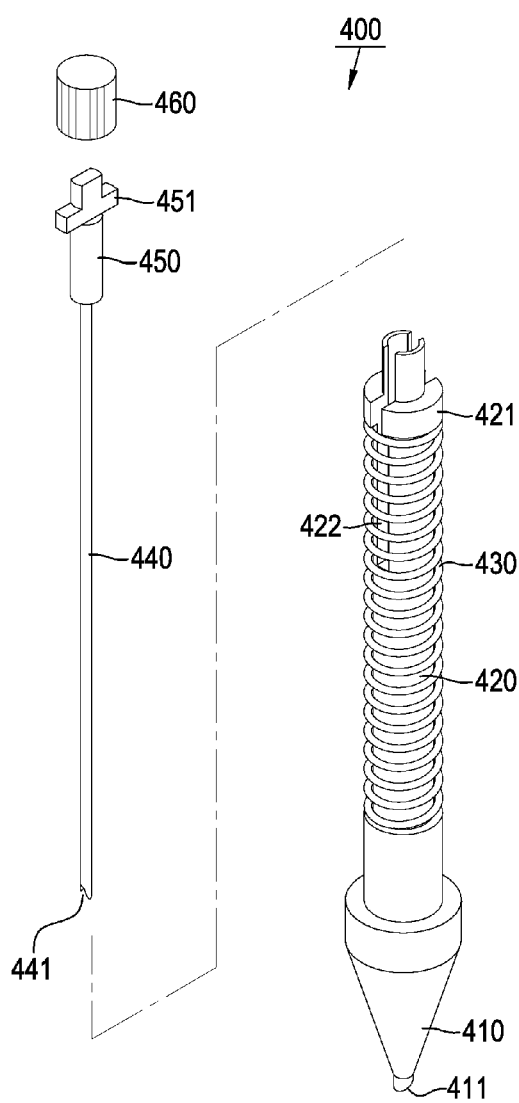
FIG. 4 is an enlarged view illustrating a head part of an implant device according to an embodiment of the present invention.

As shown in FIGS. 3 and 4, the implant device 100 is a dedicated device for the artificial hair 500, which has a shape of a pen to implant the artificial hair 500 into the scalp.

The implant device 100 may include a body part 200, a head part 400 disposed at the front end of the body part 200, and a button part disposed at the rear end of the body part 200.

The body part 200 includes a hollow body 210, and the hollow body 210 is formed such that both ends, i.e., the front end and the rear end thereof are opened in communication with each other.

The body 210 is a part of the implant device 100 which a user grips by hand when the artificial hair 500 is implanted, and is formed to have a certain length such that there is no inconvenience in gripping the implant device 100.

As shown in FIGS. 3 and 4, the head part 400 is disposed at the front end of the body 210. That is, the head part 400 includes a head 410 fixedly coupled to the front end of the body 210, an implant needle 440 withdrawably disposed at the front end of the head 410, and a first return spring 430 disposed between the implant needle 440 and the head 410 to return the implant needle 440 withdrawn from the head 410 to the original position.

The head 410 is formed to have an inclined surface 411 such that the front end thereof is inclined in an oblique direction, and the rear end of the head 410 is detachably screwed to the front end of the body 210.

In particular, the inclined surface of the head 410 is formed to be inclined at an angle of about 45 degrees, and a long end portion 411a and a short end portion 411b are formed at both sides of the inclined surface 411.

Figure 8:
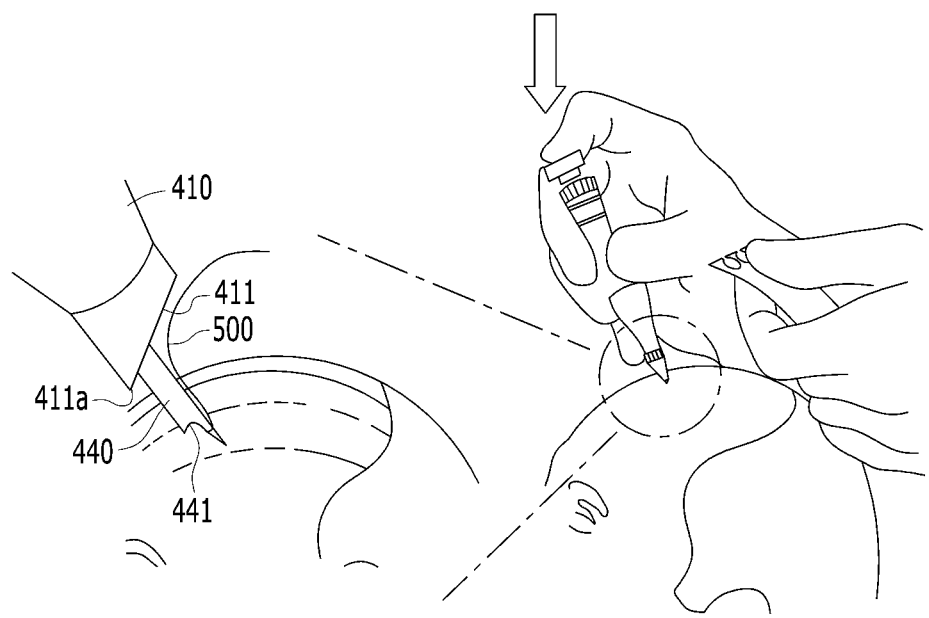
FIG. 8 is a view illustrating a state in which an artificial hair is implanted on the scalp using an implant device according to an embodiment of the present invention.

The inclined surface 411 of the head 410 secures a minimum discrimination space that enables a user to determine the state of the implant needle 440 withdrawn from the head 410 when implanting the artificial hair 500 in the scalp. That is, as shown in FIG. 8, when the artificial hair 500 is implanted, the implant device 100 is inclined to the scalp side while the long end portion 411a of the head 410 is in contact with the scalp, allowing an angle between the short end portion 411b and the scalp to be an obtuse angle. Thus, it is possible to easily determine whether or not the artificial hair 500 and the implant needle 440 withdrawn from the head 410 maintain proper positions.

In addition, a boss for screw-coupling to the body 210 may protrude from the rear end of the head 410, and a coupling pipe 420 may be integrally formed with the boss, or may be inserted into and fixed in the boss.

The coupling pipe 420 is formed of a hollow member, and a flange 421 is formed to protrude from a rear end portion of the coupling pipe 420 in a direction perpendicular to the axial direction.

A guide groove 422 is formed at the rear end portion of the coupling pipe 420. The guide groove 422 receives and guides a guide protrusion 451 of a coupling member 450 to be described later, which is coupled to the implant needle 440. The guide groove 422 is longitudinally formed along the axial direction from the rear end of the coupling pipe 420 toward the front end of the coupling pipe 420.

On the other hand, a first return spring 430, which is the compression coil spring, is provided on the outer circumferential surface of the coupling pipe 420. The first return spring 430 is provided such that both ends thereof make contact with the rear surface of the head 410 and the flange 421 of the coupling pipe 420. In this case, when the implant needle 440 moves, the first return spring 430 is compressed to the head 410 by the guide protrusion 451 of the coupling member 450 provided on the implant needle 440.

In addition, the implant needle 440 is a needle that enters and exits the head 410 while being inserted into the coupling pipe 420 of the head 410. Also, a hook 441 is formed at a front end of the implant needle 440, and a long end portion 441a and a short end portion 441b are formed at both sides of the hook 441.

The hook 441 of the implant needle 440 formed as described above is provided so as to enter and exit the inclined surface 411 of the head 410. In this case, the hook 441 of the implant needle 440 is provided so as to be withdrawn while being biased toward the long end portion 411a of the head 410. To this end, a hole from which the implant needle 440 is withdrawn may be formed on the inclined surface 411 of the head 410 so as to be biased toward the long end portion 411a of the inclined surface 411.

Figure 2:
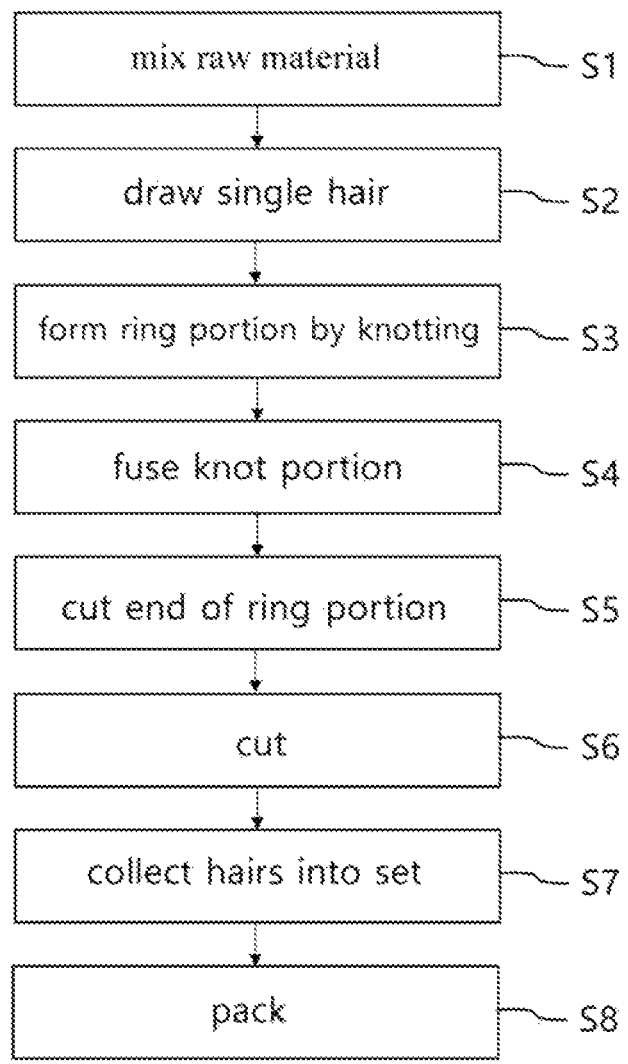
FIG. 2 is a flowchart illustrating a method for manufacturing an artificial hair according to an embodiment of the present invention.

In addition, the hook 441 of the implant needle 440 is provided such that the long end portion 441a is located at the side of the short end portion 411b of the inclined surface 411 of the head 410. This is to maximally secure the length of the long end portion 441a of the hook 441 protruding from the end of the head 410 when the implant needle 440 is inserted into the head 410 before the operation of the implant needle 440 as shown in FIG. 2.

Figure 6:
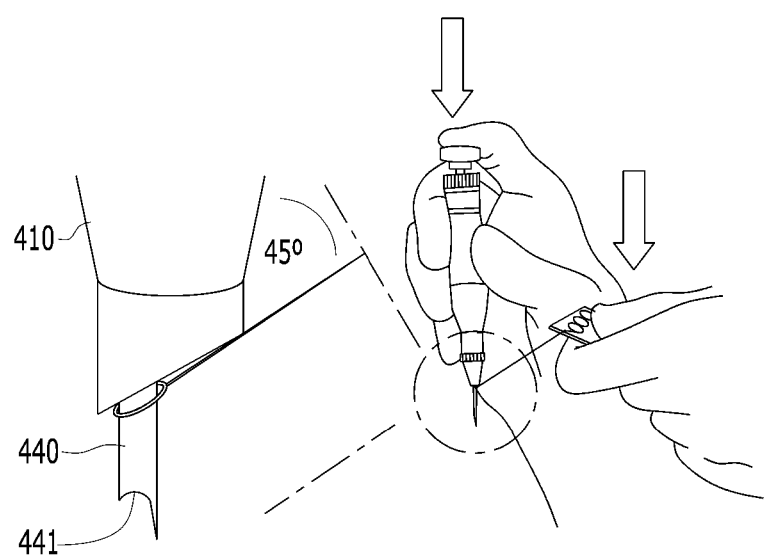
FIG. 6 is a view illustrating a state in which an artificial hair is fitted on an implant needle of an implant device according to an embodiment of the present invention.
Figure 7:
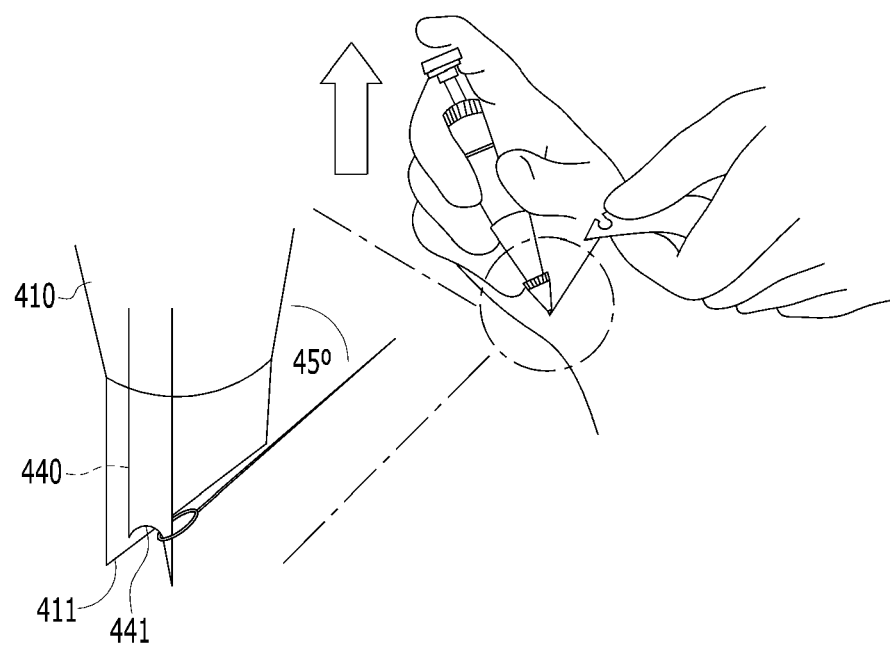
FIG. 7 is a view illustrating a state in which an implant needle of an implant device combined with an artificial hair is returned to its original position according to an embodiment of the present invention.

That is, in order to fit the artificial hair 500 on the implant needle 440, as shown in FIG. 6, the implant needle 440 is withdrawn from the head 410 to penetrate the ring portion 510 of the artificial hair 500. Thereafter, the artificial hair 500 is pulled and caught on the implant needle 440 while being in close contact with the inclined surface 411 of the head 410. Although the implant needle 440 provided with the artificial hair 500 is again inserted into the head 410 and is returned to its original position, the long end portion 441a of the hook 441 sufficiently protrudes from the inclined surface 411 of the head 410 even at the original position of the implant needle 440. Accordingly, as shown in FIG. 7, the artificial hair 500 is provided in close contact with the inclined surface 411 of the head 410, and then returns to the original position, thereby being easily caught on the long end portion 441a of the hook 441 protruding from the end portion of the head 410. However, when the hook 441 of the implant needle 440 is positioned in the opposite direction to the direction described above, that is, when the long end portion 441a of the hook 441 is located at the side of the long end portion 411a of the inclined surface 411, the artificial hair 500 cannot be caught on the hook 441 during the above-described operation because the length of the long end portion 441a of the hook 441 outwardly protruding from the head 410 in the original state in which the implant needle 440 is inserted into the head 410 is short.

Also, a coupling member 450 that is fixed to the implant needle 440 is provided at the rear end of the implant needle 440. The coupling member 450 includes guide protrusions 451 vertically protruding at both sides thereof. The guide protrusion 451 moves up and down while being inserted into the guide groove 422 of the coupling pipe 420, thereby preventing the rotation of the implant needle 440 and allowing the long end portion 441a of the hook 441 to be correctly located at the side of the short end portion 411b side of the head 410 in spite of the repeated operation.

As described above, a first ring nut 460 is coupled to the rear end portion of the coupling pipe 420 into which the implant needle 440 is inserted, thereby blocking the end portion of the guide groove 422 and thus preventing the separation of the implant needle 440.

Meanwhile, the button part 300 is configured at the rear end of the body 210. As shown in FIG. 3, the button part 300 includes a button 310 movably inserted into the rear end of the body 210 and a push shaft 311 disposed at the front end of the button 310 and pushing and withdrawing the implant needle 440 from the head 410 while entering and exiting the body 210.

The button 310 is formed of a plate for easy pressing, and the push shaft 311 is formed to protrude toward the body 210. The push shaft 311 may be formed as one shaft penetrating through a second ring nut 320 coupled to the rear end of the body 210, or may be dividedly formed as two shafts based on the second ring nut 320. On the other hand, although not shown in the drawing, in the former case, a support protrusion which is supported in contact with a second return spring 330 may be formed on a shaft located under the second ring nut 320. In the latter case, the support protrusion as described above may be formed on a lower shaft located under the second ring nut 320. The support protrusion may be caught by the second ring nut 320 to prevent the button 310 from being separated.

The second ring nut 320 is screw-coupled to the rear end of the body 210, and a hollow coupling boss 321 that is screw-coupled to the body 210 protrudes from one surface of the second ring nut 320.

In addition, the second return spring 330 is provided in the body 210 under the second ring nut 320, and both ends of the second return spring 330 are respectively supported by the body 210 and the push shaft 311 of the button 310.

Accordingly, when the button 310 is operated, the second return spring 330 is compressed by the push shaft 311 drawn into the body 210, and the tensile force of the compressed second return spring 330 serves as a restoring force for returning the button 310 to the original position.

On the other hand, the push shaft 311 of the button 310 may be provided such that the lower end thereof inserted into the body 310 makes contact with the upper end of the coupling member 450 coupled to the implant needle 440.

Then, when the second ring nut 320 is coupled to or released from the body 210, the height of the button 310 coupled thereto, that is, the length of the push shaft 311 protruding from the body 210 can be adjusted. Accordingly, it is possible to adjust the length of the implant needle 440 withdrawn from the head 410.

Hereinafter, an implant process of artificial hair according to an embodiment of the present invention will be described.

Figure 5:
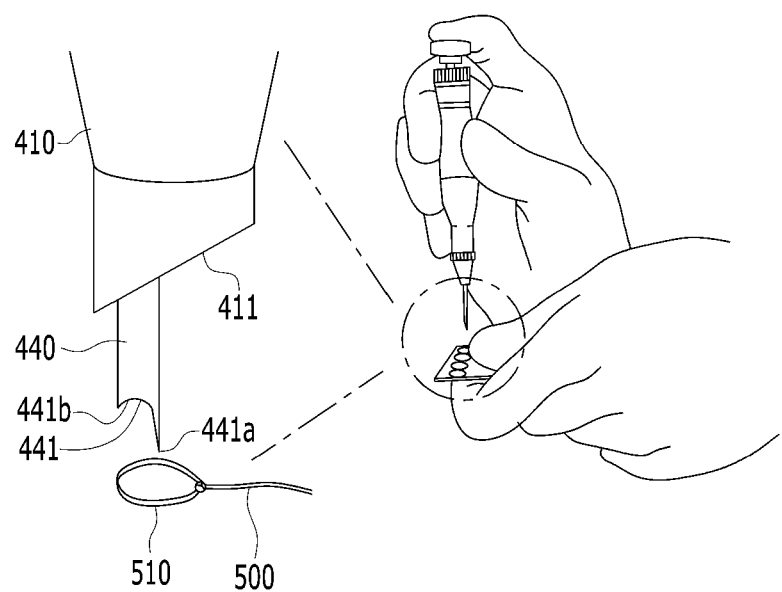
FIG. 5 is a view illustrating a process of fitting an artificial hair on an implant needle of an implant device according to an embodiment of the present invention.

First, as shown in FIG. 5, when the button 310 of the implant device 100 is pressed, the push shaft 311 descends together with the button 310 to be inserted into the body 210. The implant needle 440 is pressed by the push shaft 311 to descend in the coupling pipe 420 while the hook 441 of the implant needle 440 protrudes outward through the inclined surface 411 of the head 410.

In this case, the first and second return springs 430 and 330 are compressed by the implant needle 440 and the push shaft 311, respectively.

In this state, as shown in FIG. 6, the implant needle 440 withdrawn from the head 410 penetrates the ring portion 510 of the artificial hair 500, and then the artificial hair 500 is pulled to be coupled and fixed to the implant needle 440 while being in close contact with the inclined surface 411 of the head 410.

Then, as shown in FIG. 7, when an external force is removed from the button 310 that is pressed, the implant needle 440, the button 310, and the push shaft 311 ascend in the coupling pipe 420 and the body 210 by the tensile force of the first and second return springs 430 and 330 to return to the original positions, respectively.

In particular, as the implant needle 440 ascends into the coupling pipe 420 in the return process, the hook 441 withdrawn out of the head 410 is inserted into the head 410, but the long end portion 441a of the hook 441 is not completely inserted into the head 410. Since the long end portion 441a of the hook 441 protrudes from the head 410 by a certain length, the ring portion 510 of the artificial hair 500 is caught by the long end portion 441a of the hook 441 which is protruded.

After the implanting device 100 provided with the artificial hair 500 is brought to the target part, the implant device 100 is inclined while the long end portion 411a of the inclined surface 411 of the head 410 is in contact with the scalp as shown in FIG. 8. In a state where the short end portion 411b of the head 410 and the scalp are spread at an obtuse angle, the button 310 of the implanting device 100 is again pushed to withdraw the implant needle 440.

Then, the needle 440 that is withdrawn is inserted into the hairy fascia through the scalp, i.e., the epidermis, the dermis, and the subcutaneous tissue while the implant needle 440 is combined with the ring portion 510 of the artificial hair 500.

Figure 9:
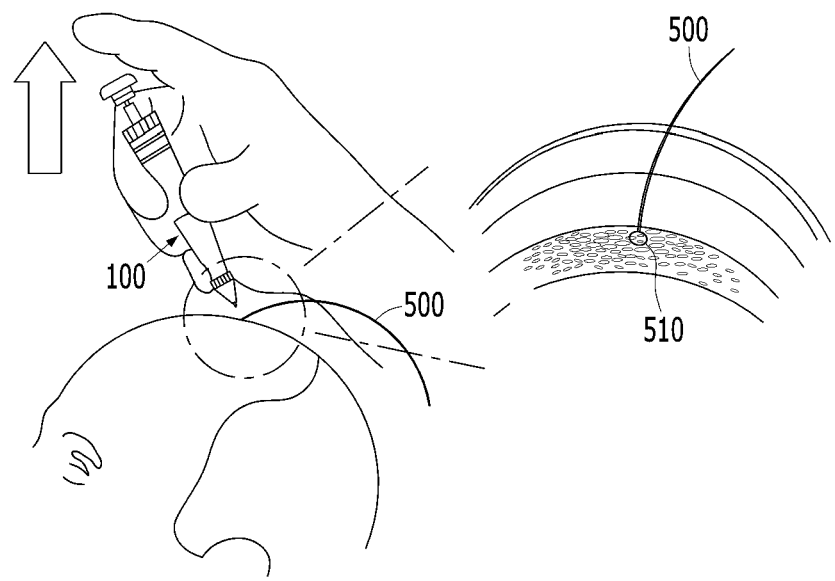
FIG. 9 is a view illustrating an artificial hair implanted using an implant device according to an embodiment of the present invention.

In this state, as shown in FIG. 9, when the implant needle 440 is returned to its original position by removing the external force pressing the button 310, the hook 441 of the implant needle 440 exits and returns from the hairy fascia. However, the ring portion 510 of the artificial hair 500 inserted into the hairy fascia is fixed and implanted in a state of being embedded in the hairy fascia.

Accordingly, the artificial hair 500 can be quickly and easily implanted into the scalp using the implant device 100 according to an embodiment of the present invention.

On the other hand, the artificial hair 500 implanted in the scalp as described above is directly inserted and buried into the hairy fascia while the ring portion 510 of the one end portion thereof penetrates the epidermis, the dermis, and the subcutaneous tissue of the scalp. Thus, rejection reaction of the human body is minimized, and the ring portion 510 of the artificial hair 500 implanted in the hairy fascia is firmly implanted and maintained in the hairy fascia based on the characteristics of the shape (since the hairy fascia completely covers the inner and outer sides of the circular ring portion 510), thereby allowing the artificial hair 500 implanted in the scalp not to be lost even when used for a long time.

Although the present disclosure has been described in detail through specific examples, it is intended to describe the present disclosure in detail, and the present disclosure is not limited thereto. Also, it is obvious that modifications and improvements by those skilled in the art are possible within the technical spirit of the present disclosure.

Simple modifications and changes of the present disclosure all fall within the scope of the present disclosure, and the specific scope of protection of the present disclosure will be apparent from the appended claims.

What is claimed is:

1. A method of manufacturing an artificial hair to be implanted in a scalp, the method comprising:
    mixing polyamide 6 powder and a master batch in a certain weight ratio;
    drawing the artificial hair from a mixture of the polyamide 6 powder and the master batch;
    forming a ring portion by knotting an end of the drawn artificial hair;
    cutting the end of the artificial hair, leaving about 1 mm to about 1.5 mm from a knot portion of the ring portion;
    cutting the artificial hair into a certain length after the cutting of the end of the artificial hair; and
    collecting a plurality of cut artificial hairs into a set, wherein:
    the ring portion is inserted and buried into a hairy fascia of the scalp;
    the diameter of the ring portion is set within a range of about 0.6 mm to about 1.2 mm such that the ring portion is insertable into the hairy fascia;
    the ring portion is coupled to the hairy fascia;
    the artificial hear is implanted using an implant device comprising
    a body part having a hollow body; a head part comprising a head coupled and fixed to the body, an implant needle provided to enter and exit the head while the artificial hair is fitted on an end portion drawn from the head, and a return spring disposed between the implant needle and the head to return the implant needle drawn from the head to the original position; and a button part movably provided in the body and a push shaft pressing the implant needle to draw out from the head while entering and exiting the body,
    wherein the head has an end portion thereof making contact with the scalp and having an inclined surface, and the implant needle entering and exiting the inclined surface of the head is drawn while being biased to a long end portion of the head, and
    wherein the implant needle has a hook formed at an end portion thereof entering and exiting the head, and a long end portion of the hook is located at a short end portion of an inclined surface of the head.

2. The method of claim 1, wherein the polyamide 6 powder and the master batch in the mixing of the polyamide 6 powder and the master batch is mixed in a weight ratio of about 90 to 100:about 10 to 0.

3. The method of claim 2, wherein the master batch is further mixed with a pigment, and the pigment comprises any one or two or more of black, yellow and red dyes.

4. The method of claim 1, wherein in the forming of the ring portion, the ring portion is formed by two or more knot portions, and the knot portion is ultrasonically fused and fixed.

5. An artificial hair manufactured by the method of claim 1.

* * * * *